United States Patent [19]
Michelson

[11] Patent Number: 5,250,061
[45] Date of Patent: Oct. 5, 1993

[54] RING CURRETTE

[76] Inventor: Gary K. Michelson, 438 Sherman Canal, Venice, Calif. 90291

[21] Appl. No.: 550,122

[22] Filed: Jul. 9, 1990

Related U.S. Application Data

[63] Continuation of Ser. No. 241,463, Sep. 8, 1988, abandoned.

[51] Int. Cl.5 ............................................. A61B 17/56
[52] U.S. Cl. ...................................... 606/160; 606/84
[58] Field of Search .................. 606/84, 160, 167, 79; 128/757, 758

[56] References Cited

U.S. PATENT DOCUMENTS 2,715,899  8/1955  MacLean ............................ 128/758
2,876,777  3/1959  Kees ................................... 606/84

OTHER PUBLICATIONS

Mueller The Surgical Armamentarium p. 627 (1980).

Primary Examiner—Michael H. Thaler
Attorney, Agent, or Firm—Lewis Anten

[57] ABSTRACT

An improved ring currette for the removal of pathological body tissues is disclosed.

3 Claims, 5 Drawing Sheets

RING CURRETTE

This is a continuation of application Ser. No. 07/241,463, filed on Sep. 8, 1988, now abandoned.

BACKGROUND

A curette is a surgical instrument consisting of a handle, a shaft, and a tip which is generally cup shaped, much like a small spoon, used for the purpose of scraping and scooping out various pathological (diseased) bodily tissues, such as a disc between two vertebrae. The open space of the cup-like tip has a sharpened rim to enhance its effectiveness for scraping.

In practice, the tip of the instrument is placed into the area of tissue to be removed and scraped against the tissue. When the cup is filled the instrument is removed from the wound and the tissue within the cup is then manually emptied. The instrument is then returned to the wound, where the process is performed repeatedly until the entirety of the pathological tissue has been removed.

A ring curette is a particular type of curette in which the cup is without a bottom, forming a ring. While such a curette is less useful in scooping out and removing scraped tissues, this is more than offset by its enhanced effectiveness in the more specific task of scraping the tissue free. Since the bottom of the cup is absent, the scraped tissue passes through the ring and does not accumulate in the cup, allowing the instrument to continue scraping. As large amounts of tissue once freed can more easily be removed with a surgical instrument known as a rongeur, it is more efficient to utilize the ring type curette followed by use of the rongeur, rather than using the cup type curette.

Furthermore, since the ring curette and the rongeur are more specialized to their singular purposes, they are more effective. Also, since they require less frequent passing of the instrumentation in and out of the body, with the attendant risk of internal tissue injury and wound contamination, they are also safer.

DESCRIPTION OF THE PRIOR ART

FIGS. 1A, B and C show a representative conventional prior art ring curette. The prior art tip has a complete uninterrupted circular scraping rim. The junction between the tip and the shaft is consisting of a relatively finely tapered distal shaft which is easily manufacturable and is relatively weak. Pressing this narrow shaft against a vertebra could result in damage to the vertebra or damage to the shaft. The prior art ring curette has no mechanism for measuring the depth of penetration of its tip in the wound.

SUMMARY OF THE INVENTION

The present invention is a more effective ring curette for safely and easily scraping tissue. The shaft of the ring curette of the present invention is circular at its end connected to the handle and has a wide flat surface having marks near the junction of the shaft and the tip for measuring the depth of penetration of the tip.

The wide surface of the shaft permits using the ring curette in the manner of a lever, having its fulcrum on the vertebra. This makes scraping easier, while avoiding damage to the vertebra. This levering action is also assisted by having the handle of the curette sufficiently large so as to enable the handle to be grasped fully by both hands at the same time.

The ring tip has a discontinuous scraping rim surface so that scraping action is achieved only by the forward interior portion of the ring tip. This is in contrast to the prior art conventional ring tip structure which has a scraping rim surface around the entire inner portion of the ring tip. Since the rear portion of the ring tip of the present invention is depressed, when the ring tip is pushed back and forth to scrape the tissue, tissue cannot catch on the rear portion of the ring tip.

OBJECTS OF THE INVENTION

It is an object of the present invention to provide for an improved surgical ring curette, which is more effective for scraping tissue.

It is another object of the present invention to provide an improved surgical ring curette which is safer.

It is another object of the present invention to provide an improved surgical ring curette which is easier to use.

It is still another object of the present invention to provide a ring curette that is more durable.

It is yet another object of the present invention to provide an improved surgical ring curette that provides a visual indication of the position of the cutting tip of the ring curette.

These and other objects of the present invention will be apparent from a review of the following specification and accompanying drawings.

DETAILED DESCRIPTION OF THE DRAWINGS

Figure 1A:
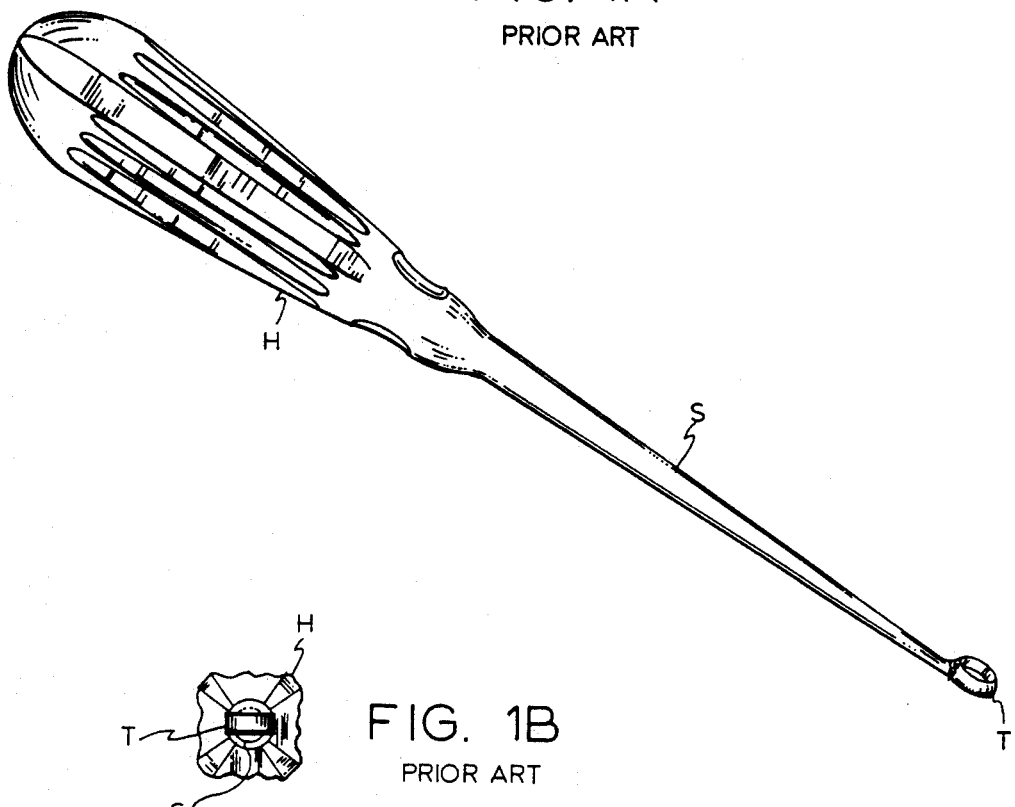
FIG. 1A is a perspective view of a conventional prior art ring curette.
Figure 1B:
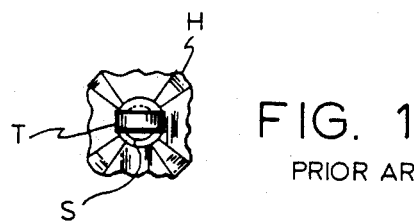
FIG. 1B is an end view of the prior art ring curette of FIG. 1A.
Figure 1C:
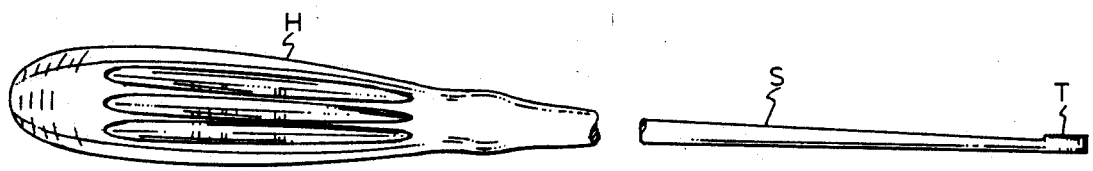
FIG. 1C is a side view of the prior art ring curette in of FIG. 1A.
Figure 1D:
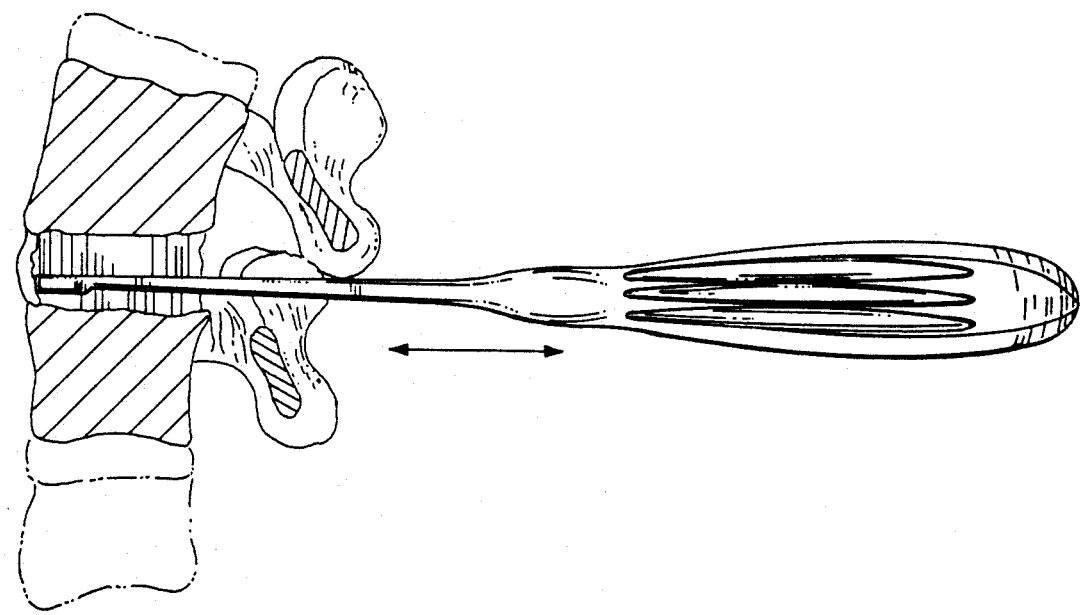
FIG. 1D is a side view of a prior art rint curette in a vertebral interspace.

FIGS. 1A–1C show a conventional prior art ring curette consisting if a handle "H", shaft "S", and a tip "T" essentially ring like in shape. There is extreme tapering of the shaft at the junction to the ring tip. The scraping rim of the ring tip is uniform across its entire circumference and has a uniform interior wall surface. FIG. 1D is a side view of the prior art ring curette in a lumbar interspace and parallel to the end plate consistent with its method of use.

Figure 2:
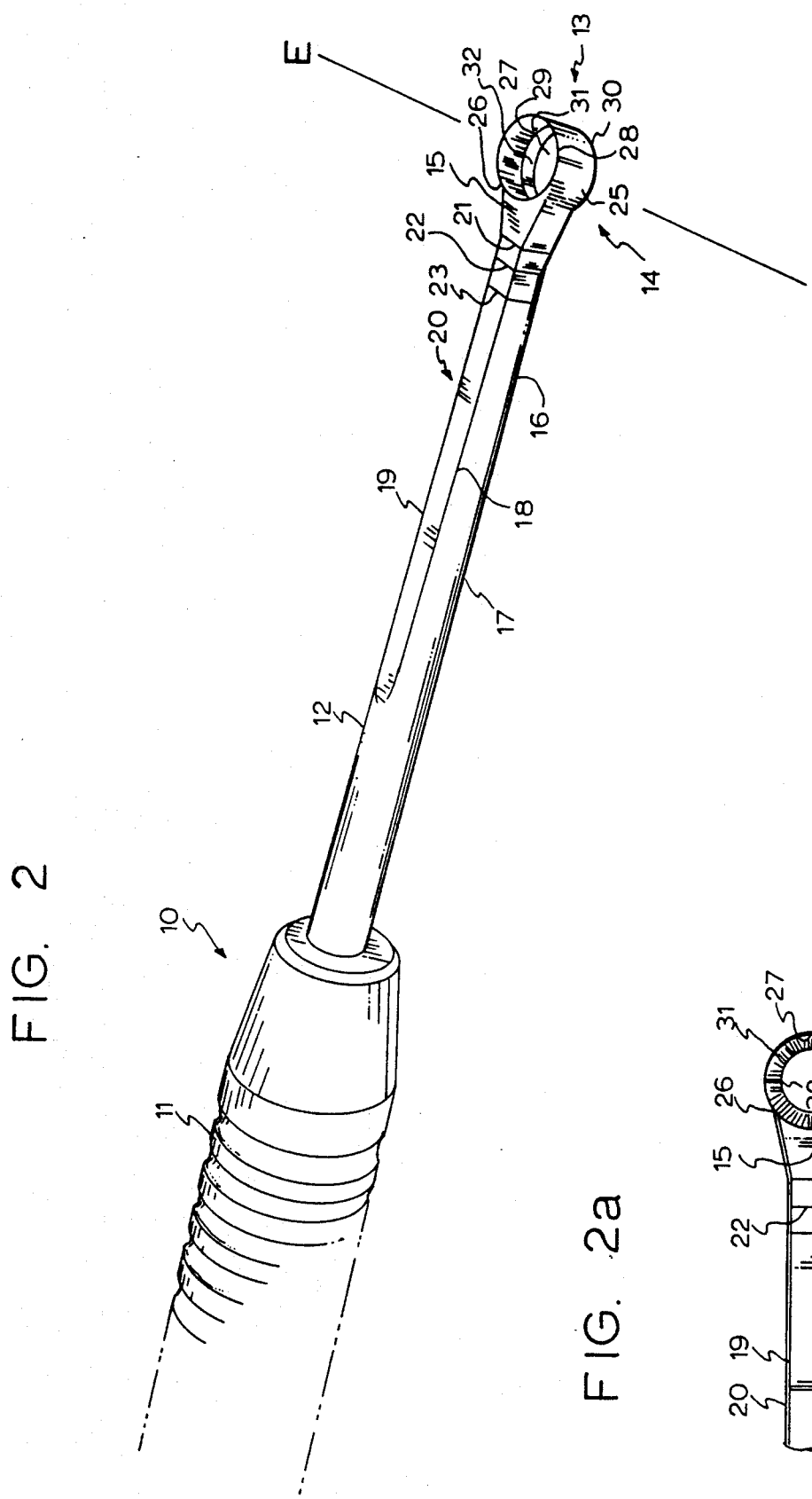
FIG. 2 is a perspective view of the present invention.
Figure 2A:
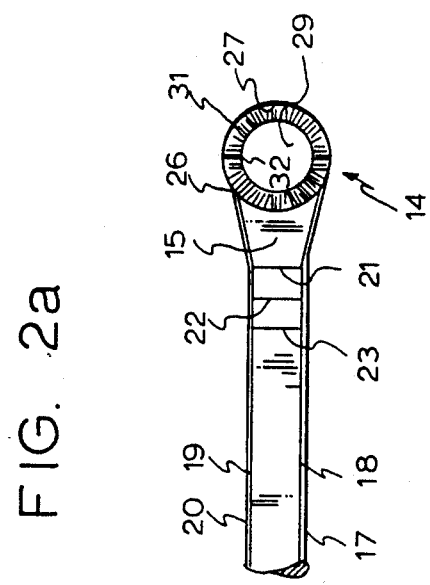
FIG. 2A is a top view of the ring curette of FIG. 2.
Figure 4:
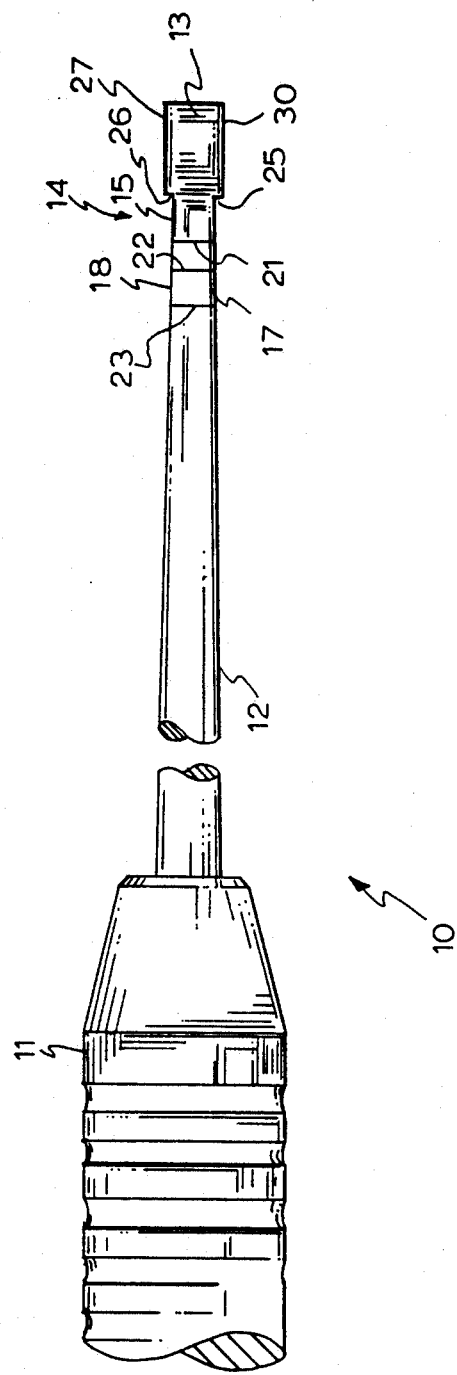
FIG. 4 is a side view of the ring curette of FIG. 2.
Figure 3:
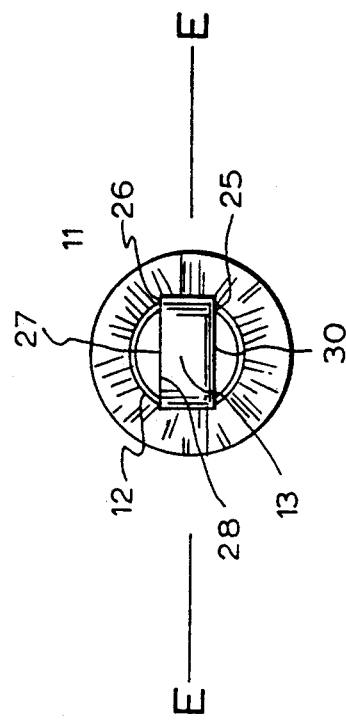
FIG. 3 is an end view of the ring curette of FIG. 2.

FIG. 2 is a perspective view of the present invention 10 consisting of handle 11, shaft 12 and ring tip 13. The distal end 14 of the shaft has opposed broad flat surfaces 15 and 16 and blunted edges 17, 18, 19 and 20 (not shown). The shaft 12 is sufficiently long to allow the handle 11 to be grasped by both hands of the user. the distal end 14 of the shaft 14 has circumferential scribe marks 21, 22 and 23 corresponding to lengths from the most distal extremity of the tip 13. The scribe marks 21, 22 and 23 are separated by 20, 25 and 30 millimeters, allowing the surgeon to assess the depth of penetration of the ring tip 13 even when the ring tip of the instrument cannot be visualized. Since the ideal depth of penetration of the ring tip 13 in the lumbar spine, for example is between 20 and 30 millimeters, it is possible to achieve that ideal without the danger of over penetration despite the fact that the tip may not be visible. The markings may be color coded segments instead of, or in addition to, the scribe marks 21, 22 and 23.

The ring tip 13 has a central opening 29, an outside major diameter which is greater than the width of the neck of the shaft 12 and greater than the inside diameter of opening 29. The upper and lower scraping rim surfaces 27 and 30 of the ring tip 13 extend above and below the broad flat surfaces 15 and 16 of the shaft 12. The upper and lower scraping rim surfaces have cut out portions 25 and 26 at the portion of the ring tip 13 proximate the junction of the shaft 12 and the ring tip 13, the junction being the point where the shaft is connected to the ring tip. The bottom of the cut out portions 25 and 26 are level with the flat surfaces 15 and 16 of the shaft 12. The portions of the upper and lower scraping rim surfaces 27 and 30 facing the opening 29 are exceedingly sharp, while the portions 28 facing away from the opening 29, are dull. The inside walls 31 of the ring tip 13 are tapered inwardly from the top and bottom so as to create a funnel effect into the opening 29. The meeting of the upper and lower sloping walls 31 is referred to as the equator 32.

In the preferred embodiment, the handle 11 has a diameter of approximately 1¼ inches and is 8½ inches long. The shaft 12 is approximately 5½ inches long and has a diameter of ⅜ inches. The ring tip has an outside diameter at the scraping rims of about ⅝ inches and about 7/16/inches at the narrow equator. The scraping rims of the ring tip have an overall height of 5/16 inches and extends approximately 1/32 inches above the plane of the flat portion of the shaft. The shaft has a width at the flat portion of ¼ inches and tapers smoothly to the side walls of the ring tip. The depressed portion extend around 90 degrees of the circumference of the ring tip.

Figure 5:
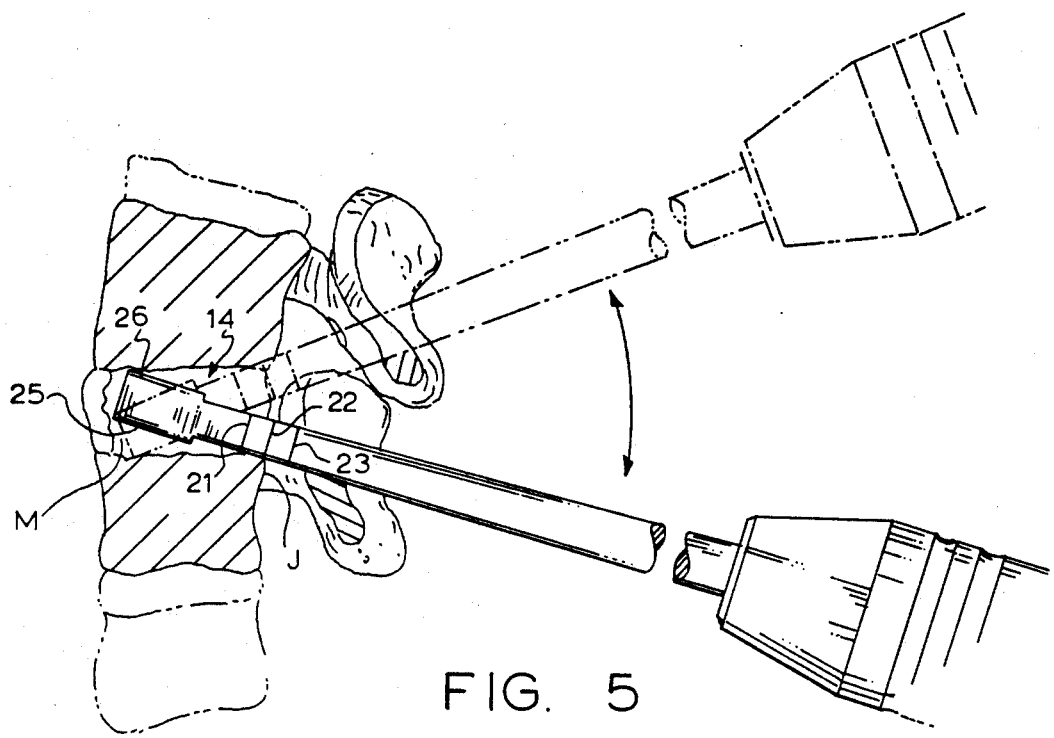
FIG. 5 is a side view of the present invention shown in a vertebral interspace.

FIG. 5 is side view of the present invention in a lumbar disc space showing the placement if the distal shaft 14 with depth markings 21, 22 and 23 against the vertebral endplate body junction J. The orientation of the instrument is shown being utilized with the scraping rim of ring 24 scraping the disc material M, facilitating its removal.

Since the ring tip 13 is open across its widest area the tissue is essentially funneled by the sloping interior walls into a trapped position where it is easily sheared by the advancing sharpened inner edge.

Since the scraping rim of the ring tip is dull on its outer edge and offers a closed ring most distally, it cannot accidentally penetrate too deeply and will cut tissue only on the upstroke. Since the more proximal end of the ring tip does not have a sharpened and protruding scraping rim, as the tip is brought from deep to superficial on the cutting stroke, the more superficial tissues including the spinal sac and nerve roots will not be accidentally cut by the ring tip.

Also, conventional ring curette require the operator to use considerable force to resist the tendency of the full ring tip to be pushed away by the rear tissue. There is an ever present and real danger that the grasp on the rear tissue will give way, or that the ring tip will slide off, and plunge through the front of the disc rupturing the aorta, venae cava, or other vital structures and possibly causing the death of the patient. Also, for the very same reasons it is possible for the conventional ring tip curette to lose engagement on the upstroke and to forcefully escape the disc space posteriorly (from behind) rupturing the dural sac and possibly causing paralysis.

The present invention is more effective in engaging the tissue because the depressed rear portion prevents it from catching on the tissue. Further, the depressed portion of the scraping rim of the ring tip becomes fully visible prior to the cutting edge arriving, thereby allowing the operator to avoid accidental presentation.

A further safety design feature is that the ring tip is closed to slightly beyond the equator of the ring tip so that by rotating the ring tip, moving the shaft from the vertical to a more horizontal position, it is then possible to extract the ring tip without having the cutting edge of the protruded rim engage the surrounding tissues, thereby avoiding damage those tissues.

The relatively large mass of the shaft tip junction without a narrow neck, allows the instrument to be safely utilized without mechanical failure. The broad and flattened surfaces parallel to the open faces of the ring tip and to the vertebral endplates, combined with the blunted edges, is designed to protect the vertebrae themselves by providing a large surface area without any sharp edges. The prior art ring curette cannot be used in this manner (leveraged off the fulcrum of the vertebral body endplate junction) because they are not sufficiently strong and are delicately necked at the ring and shaft junction. Such levering with a slender and rounded shaft would result in too small an area for such a magnitude of load and would result in either a fracturing of the vertebra or a failure of the instrument.

Finally, the prior art shaft with its tapered neck offers no resistance to the movement of the instrument in and out of the wound. Thus, as the operator attempts to insert the ring tip through the small opening of the interspace, there is an increasing resistance as the major diameter of the ring tip is approached, and then a sudden plunging, and giving way. Similarly, on attempting to remove the instrument, there is an increasing resistance as the major diameter of the ring tip is approached, and then a sudden release and "flying away" of the instrument.

In contrast, the present invention has a confluent junction of tip and shaft which allows for the smooth introduction and removal of the ring tip.

FIG. 1D demonstrates the method of use of the prior art ring curette while FIG. 5 demonstrates the method of use of the present invention. The present invention takes advantage of the available vertebra and employs the very strong cortical bone at the vertebral body endplate junction as a fulcrum point. Since the distance from the fulcrum to the tip is considerably shorter than the distance from the fulcrum to the handle, a mechanical advantage is produced which increases the effectiveness of the instrument an greatly reduces the amount of force needed to be applied t the handle to obtain effective tissue cutting. The large diameter and long handle permits the instrument to be held by both of the surgeons hands, thereby permitting better control of the instrument during the scraping activity.

Figure 6:
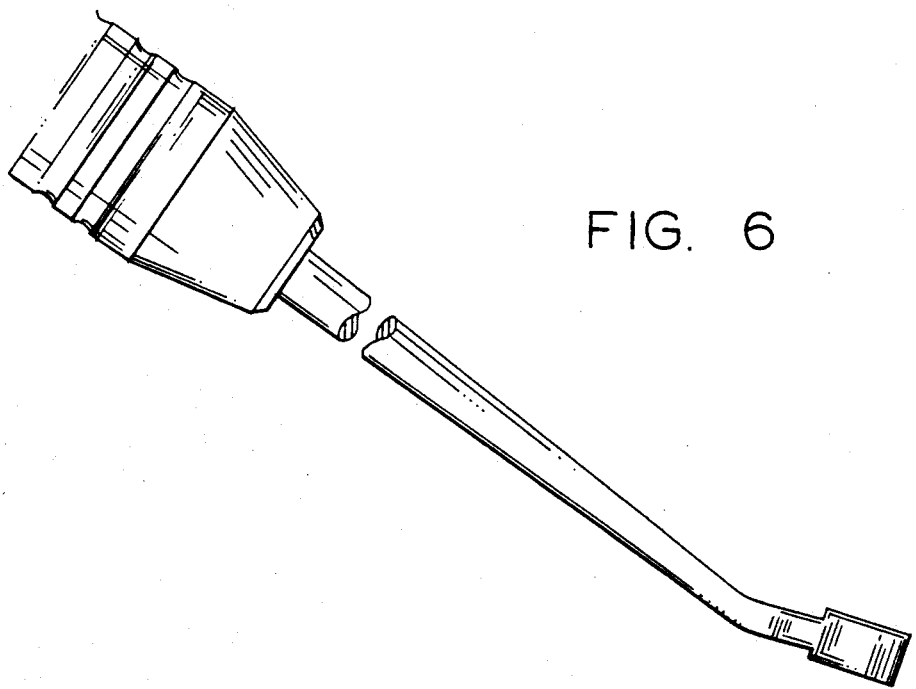
FIG. 6 is a side view of an alternative embodiment of the present invention.

FIG. 6 is an alternative embodiment of the present invention with the distal shaft angled to facilitate the removal of disc tissue in a more angulated interspace.

While the examples offered refer to the use of the present invention in the spine, such instruments would be useful in many other areas of the body. Also, while the tip and shaft of the present invention may be made of an appropriate surgical quality metal, it is recognized that the tip and shaft as well as the handle might be made from non-metallic but equivalent materials, such as plastics, ceramics, composites, or other.

Also, while the ring curette of this present invention has been described in relation to a ring curette having sharp scraping rim surfaces on both the upper and lower surfaces of the ring tip, it can be employed on only one of the surfaces.

What I claim is:

1. A ring curette comprising a straight shaft having a first end and a second end, a handle attached to said first end and a scraping tip attached at said second end, said scraping tip in the shape of a ring, said handle being large enough so as to permit grasping of the handle by two hands, said shaft having flattened top and bottom portions in planes parallel to the plane of the ring proximate the connection of the scraping tip to the second end of said shaft, said ring extending above the planes of said flattened portions of said shaft, the circumference of said ring being sharpened, said ring having a depressed portion proximate the connection of the scraping tip to said second end of said shaft, an edge of said depressed portion being in the plane of a flattened portion of said shaft and in which said ring has an interior opening forming side walls, said opening having a central portion which is smaller in diameter than the inside diameter of said ring at either the top or bottom of said ring, the inside walls of said ring sloping towards the center of said opening.

2. The ring curette of claim 1 in which said handle has a diameter greater than 1 inch and a length of at least 5 inches.

3. The ring curette of claim 1 in which the ring curette is symmetrical about its central axis in the plane of said ring.

* * * * *